(12) United States Patent
Guillermo

(10) Patent No.: US 9,132,241 B2
(45) Date of Patent: Sep. 15, 2015

(54) INJECTION DEVICE WITH DAMPENING MECHANISM

(75) Inventor: Carlos Guillermo, Los Osos, CA (US)

(73) Assignee: SHL Group AB, Nacka Strand (SE)

( * ) Notice: Subject to any disclaimer, the term of this patent is extended or adjusted under 35 U.S.C. 154(b) by 337 days.

(21) Appl. No.: 13/126,565

(22) PCT Filed: Oct. 6, 2009

(86) PCT No.: PCT/EP2009/062938
§ 371 (c)(1),
(2), (4) Date: May 10, 2011

(87) PCT Pub. No.: WO2010/049239
PCT Pub. Date: May 6, 2010

(65) Prior Publication Data
US 2011/0213314 A1    Sep. 1, 2011

(30) Foreign Application Priority Data
Oct. 29, 2008    (SE) ...................... 0850058

(51) Int. Cl.
*A61M 5/32*    (2006.01)
*A61M 5/20*    (2006.01)
*A61M 5/31*    (2006.01)
*A61M 5/46*    (2006.01)

(52) U.S. Cl.
CPC ........... *A61M 5/3232* (2013.01); *A61M 5/2033* (2013.01); *A61M 5/46* (2013.01); *A61M 2005/206* (2013.01); *A61M 2005/208* (2013.01); *A61M 2005/2086* (2013.01); *A61M 2005/3143* (2013.01)

(58) Field of Classification Search
CPC ............ A61M 5/3232; A61M 5/2033; A61M 2005/206; A61M 2005/3143; A61M 2005/2086
USPC .................. 604/110, 192, 198, 218, 228, 230
See application file for complete search history.

(56) References Cited

FOREIGN PATENT DOCUMENTS

EP    1 743 666    *    1/2007
GB    2 424 838    *    10/2006

* cited by examiner

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

An injection device comprising a medicament container, a needle attached to the container, and a mechanism for automatic penetration of the needle, injection of medicament and withdrawal of the needle. The device operates by initiating a penetration sequence, followed by an injection sequence and followed by a withdrawal sequence. A previous sequence can trigger a subsequent sequence. The device further comprises a dampening mechanism arranged and designed to dampen the movement of the injection mechanism during an injection sequence.

6 Claims, 10 Drawing Sheets

INJECTION DEVICE WITH DAMPENING MECHANISM

TECHNICAL FIELD

The present invention relates to an injection device and in particular an injector having several automatic functions.

BACKGROUND OF THE INVENTION

There are many injectors on the market where the aim is to have high degrees of functionality and automatic features, such as in connection with penetration, injection, setting of dose, priming and covering of the needle after use. At the same time there is a demand on robustness, repeatability and reliability regarding the function, which sometimes might be difficult to meet when dealing with complex multi functions involving many interacting components. When there further are demands on low production costs, especially for devices that are to be used only once, the picture becomes even more complex.

There are in the patent literature numerous solutions to injection devices, the bulk of which never enter the market due to that they do not meet the demands in one way or the other. There is therefore a continuous search for solutions that provide the desired functions that at the same time fulfil the functional and/or economical demands.

Many devices having multi-functions that work in sequence, such as for example penetration, followed by injection, followed by withdrawal, have a subsequent sequence triggered at the end of a previous sequence, for example when the needle has reached full penetration depth, the injection sequence is triggered.

A common design is to have the movement of an action, e.g. an injection stroke, to trigger a subsequent movement. To facilitate this in a robust way, tolerances has to accounted for and in that a trigger point will most often have to be set a portion ahead of the absolute end point. If reaching the end point it may happen that the displacement of a means that is required to trigger the subsequent action may not occur. If, on the other hand the trigger point is set too early in the stroke, the subsequent movement may be triggered so the previous action is not completed within the required time or sequence. In both cases there is a risk is that an intended action may become faulty or not occur at all.

One attempt to solve this is disclosed in document WO 03/097133 discloses a device having a plunger rod arranged in two parts movable to each other. Between the parts a delay mechanism is arranged as a piston/cylinder arrangement with a small bleed hole for evacuating the air when the parts are pressed together, whereby a delay of the movement of the plunger rod during the injection sequence is intended, which should ensure that the medicament container is emptied before the needle is retracted. However, since both penetration and injection are performed by a common spring acting on the plunger rod, the delay mechanism is working during the whole penetration and injection sequence whereby there is a pronounced risk that the delay function has terminated long before the end of the injection sequence is reached. Further, during the injection operation the retraction spring is tensioned.

The document GB 2 414 404 describes an injection device having a reservoir containing highly viscous damping fluid, one strong drive spring for performing both penetration and injection, a weaker spring that is tensioned by the stronger spring during penetration and injection for a needle retraction, and a delay means which is intended to delay the movement of the plunger rod just before the end of an injection, whereby the plunger rod is released from the drive spring and the needle is withdrawn from the injection site. The delay means comprises two decoupling mechanisms wherein the first decoupling is activated just before the stopper within the reservoir reaches its end and the second is activated just before the reservoir is emptied. The decoupling is however delayed due to the time it takes to empty the reservoir, whereby it is ensured that the remaining contents of a container is discharged before the container is released and returned to the original position. However, since the delay starts to act just before the end of the injection there is a pronounced risk that the elastic members of the injection systems, such as rubber compounds or air that by pressure from a plunger rod has become compressed, do not have the enough time to expand to a relaxed state before the retraction is triggered and thereby causing problems with its functionality accuracy and reliability.

The document GB 2 414 404 or GB 2 424 838 or GB 2 396 298 describes an injection device comprising one strong drive spring means for performing both needle penetration and injection by acting on a stopper of a syringe, a weaker spring that is tensioned by the stronger spring during needle penetration and injection for a needle retraction, a delay means having a reservoir containing highly viscous damping fluid, which is intended to delay the movement of the plunger rod just before the end of an injection, whereby the plunger rod is released from the drive spring and the needle is withdrawn from the injection site. The delay means comprises two decoupling mechanisms wherein the first decoupling is activated just before the stopper within the syringe reaches its end and the second decoupling is activated just before the reservoir is emptied. The second decoupling is however delayed due to the time it takes to empty the reservoir, whereby it is ensured that the remaining contents of a container is discharged before the container is released and returned to the original position. However, since the delay starts to act just before the end of the injection there is a pronounced risk that the elastic members of the injection systems, such as rubber compounds or air that by pressure from a plunger rod has become compressed, do not have the enough time to expand to a relaxed state before the retraction is triggered and thereby causing problems with its functionality accuracy and reliability.

There is thus room for further improvements in the technical area of injection devices with a certain amount of automatically and reliable performed functions.

BRIEF DESCRIPTION OF THE INVENTION

The aim of the present invention is to provide an injector that fulfils the demands that are put on such devices regarding functionality, accuracy and reliability and which ensure that specific functions, such as injection, are fully completed before a subsequent function is initiated.

According to a main aspect of the invention it is characterized by the features of the independent patent claim. Further advantageous features are subject of the dependent claims.

According to an aspect of the invention an injection device includes an elongated housing; a container carrier having a medicament container to which a needle is attached; penetration means comprising a decoupling sleeve, a preloaded penetration spring means capable of acting on said decoupling sleeve and thereby on said container carrier causing a sliding movement of the container and needle, and penetration holding means capable of holding said penetration spring means in a loaded state; injection means comprising a plunger rod arranged to act on a stopper in said medicament container, a preloaded injection spring means capable of acting on said plunger rod for displacement of said stopper inside said container, and injection holding means capable of holding said injection spring means in a loaded state; withdrawal means comprising a preloaded retraction spring arranged to act on said decoupling sleeve and thereby on said container carrier, and withdrawal holding means capable of holding said retraction spring in a loaded state; means for initiating a penetration sequence capable of acting on a penetration trigger means which is arranged on said decoupling sleeve for disconnecting said penetration holding means; injection trigger means arranged on said decoupling sleeve and capable of disconnecting said injection holding means for initiating an injection sequence when the decoupling sleeve and the plunger rod have moved to a certain position; and withdrawal trigger means arranged on said decoupling sleeve and capable of disconnecting said withdrawal holding means for initiating a needle withdrawal when said plunger rod has moved to a certain position; wherein the device further comprises a dampening means comprising a compartment containing a volume of highly viscous liquid and defined in part by the outer surface of the plunger rod and an inner surface of a cap, wherein said compartment is arranged with a passage through which the liquid may be forced only when the injection sequence is initiated, such that the volume within the compartment decreases as the plunger rod moves within the container during the whole injection sequence and thereby creating a dampening shear force.

According to another aspect of the invention, the passage ends in the interior of the plunger rod.

According to yet another aspect of the invention, the passage ends in an annular space created between said plunger rod and the inner surface of the medicament container, whereby said highly viscous liquid is capable of creating a dampening shear force.

According to a further aspect of the invention, the means for initiating a penetration sequence comprises an activation button, a penetration sleeve, a lockout sleeve and a needle shield wherein said lockout sleeve is arranged and designed to allow said penetration sleeve to interact with said penetration trigger means for initiating the penetration sequence after said needle shield is pressed against an injection site and said push button is manually operated The advantage with the device according to the present invention is for one that a dampening of the movement of the plunger rod during the whole injection sequence ensures that a complete injection is obtained before a subsequent step, i.e. the withdrawal of the needle, is triggered. This provides an increased reliability regarding complete emptying of the medicament container, without increasing the tolerance and functional demands on the interacting components.

The reliability in performing the injection is also increased because the withdrawal spring is not affected at all during neither penetration nor injection, but it rests in its loaded state until the penetration and injection sequences are completed and those spring means are decoupled and only after this is the withdrawal activated. This is in contrast with the above mentioned devices which both rely on the withdrawal spring being tensioned because of the force and the movement of the injection mechanisms. The counter-directed spring forces, together with friction and tolerance miss-match between co-acting components, could result in an uncompleted injection sequence, i.e. that a lesser dose than prescribed is injected.

Because the delaying is performed by highly viscous liquid being pressed through a passage, a reliable and controlled function is obtained. The delay mechanism is preferably arranged at the front end of the plunger rod, whereby the passage could end in the interior of the plunger rod. However, it is to be understood that the passage may end in other spaces of the injection device, for example in the annular space between the plunger rod and the inner surface of the tubular medicament container. In this way the highly viscous liquid could also act as a damper creating dampening shear forces.

Grease viscosity and hydraulic diameter, size and shape of the opening of the plunger rod, are main parameters to tune to deliver the intended and desired functionality, the intended function being to achieve a time delay at stroke end so that displacement members of the system are not triggered before desired displacements, such as e.g. delivery of the drug, have been completed.

The solution provides a cost effective multi-function device comprising a safe and reliable chain of sequences, thus ensuring that the user receives a proper dose of medicament each time the device is used.

These and other features and advantages with the present invention will become apparent from the following detailed description and the drawings.

BRIEF DESCRIPTION OF THE DRAWINGS

In the following detailed description, reference will be made to the drawings, of which

DETAILED DESCRIPTION OF THE INVENTION

Figure 1:
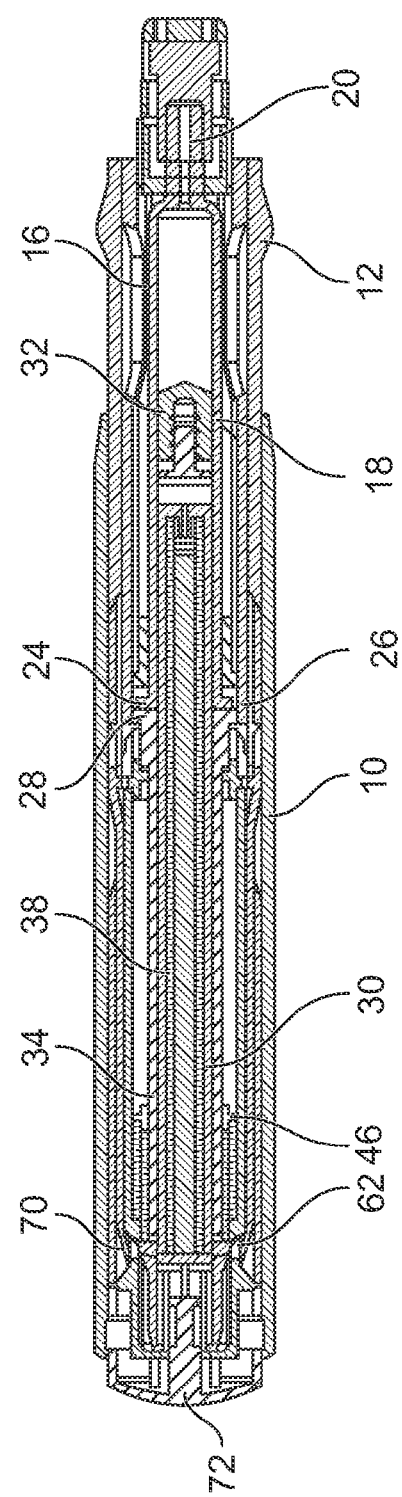
FIG. 1 is a longitudinal cross-section of an injector comprising the present invention.
Figure 2:
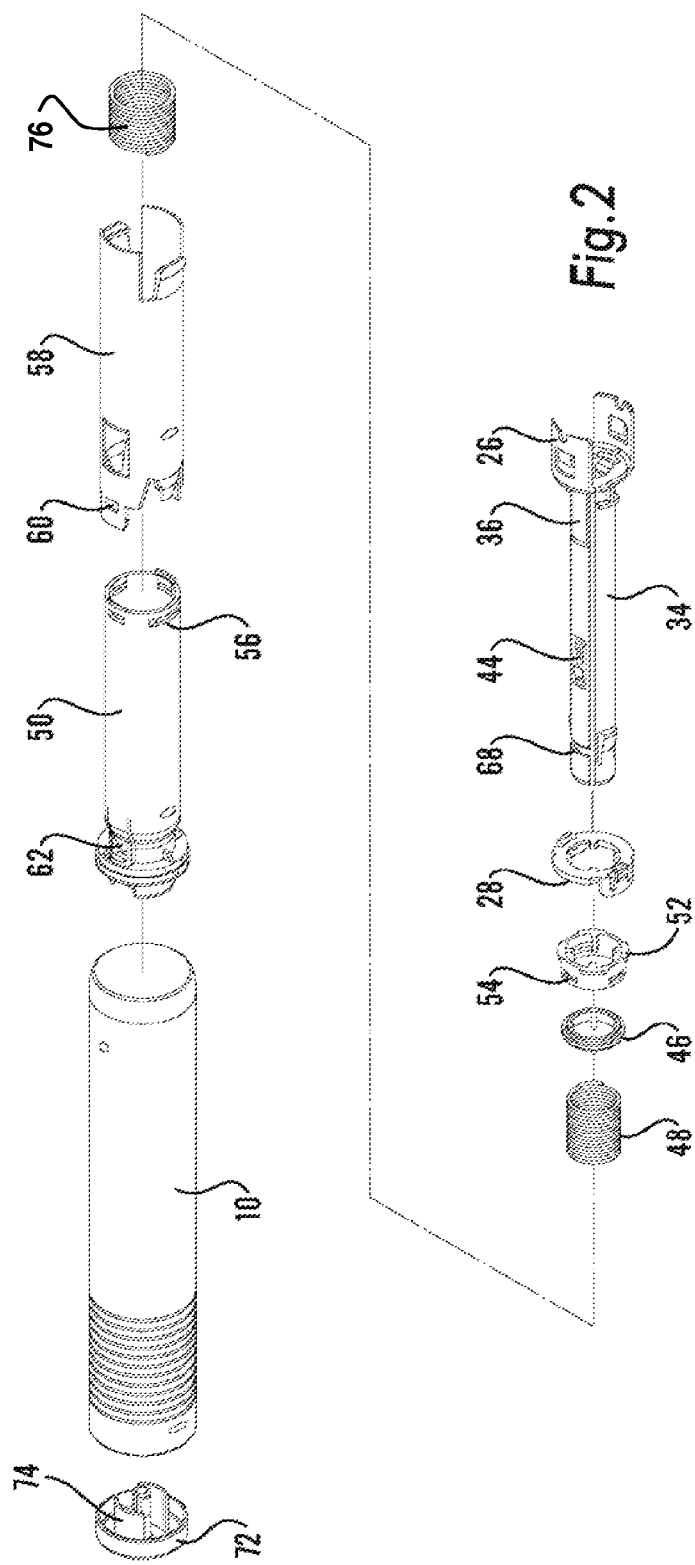
FIGS. 2-3 are exploded views of the injector of FIG. 1.
Figure 3:
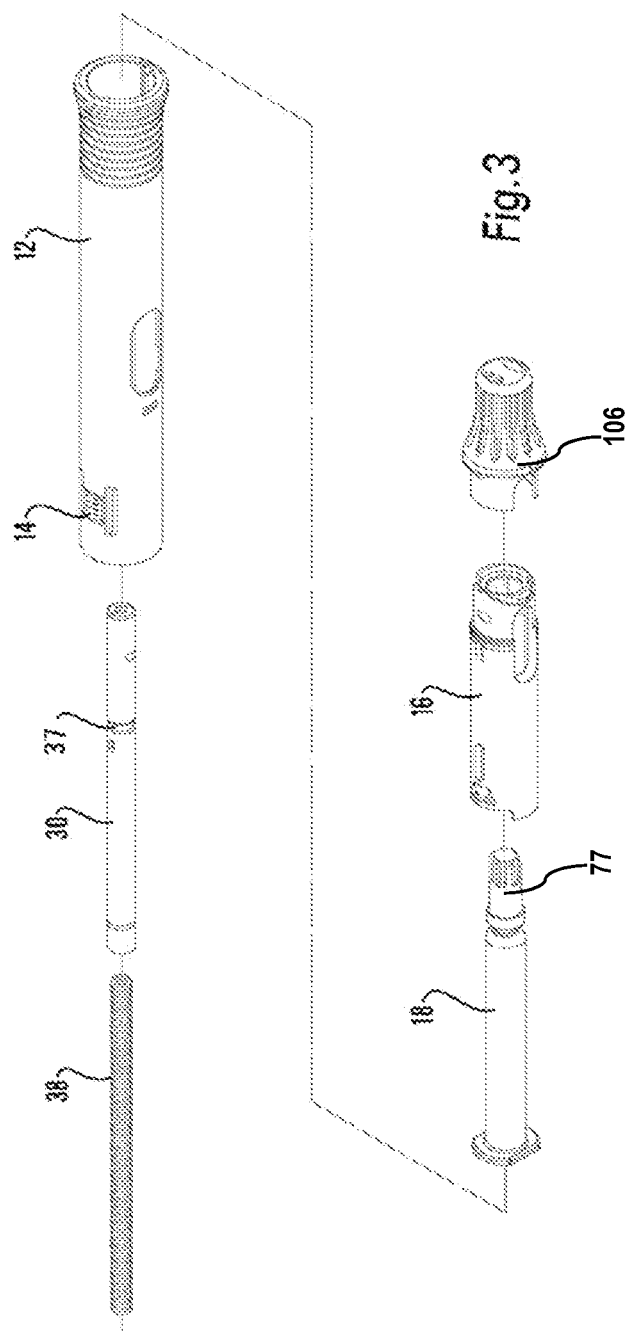
Figure 5A:
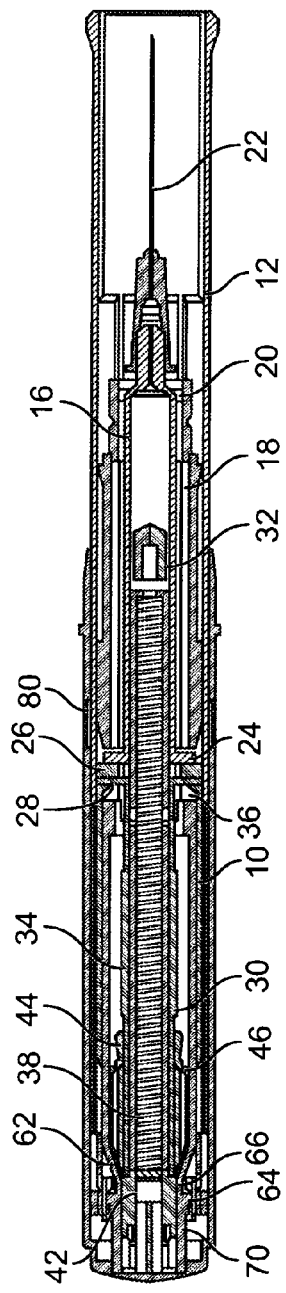
FIGS. 5A, 5B, 6, 7, 8, and 9 show different functional steps of the device of FIG. 1.
Figure 5B:
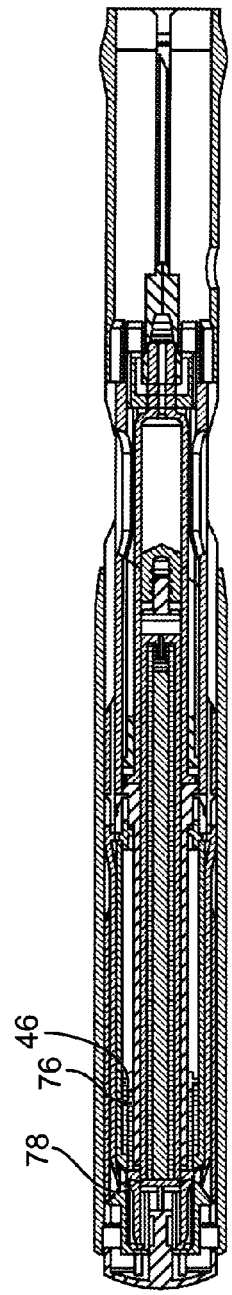

The device according to the figures comprises a generally tubular outer housing 10. In the front end of the housing, to the right in FIG. 1, a generally tubular needle shield 12 is arranged slidably in the outer housing. When in the non-extended position the needle shield is held in place by protrusions 14 on the outer surface co-operating with ledges (not shown) on the inner surface of the housing. Inside the needle shield in the front area of the device a container carrier 16 is arranged. Inside the container carrier a container 18, containing medicament, is attached. Container is to be interpreted as comprising syringes, cartridges, ampoules and the like. The front end of the container is arranged with attachment means 20 for attaching a needle 22 to the container. The rear end of the container is seated with its flange 24 in a holder 26. Adjacent the holder an injection release ring 28 is arranged, which will be described in more detail below. A plunger 30 extends into the container with one end adjacent a stopper 32. The rear end of the plunger is surrounded by a decoupling sleeve 34 which is snap-fitted to the container holder. The decoupling sleeve is arranged with flexible tongues 36, FIG. 2, where each tongue is arranged with inwardly directed ledges. In the initial state, these ledges are positioned in a circumferential groove 37 on the plunger 30. The tongues and ledges are held in this position by the injection release ring 28. Inside the plunger an injection spring 38 is arranged compressed between a front wall of the plunger 30 and a wall part 42 of the decoupling sleeve 34. The decoupling sleeve is further arranged with outwardly extending protrusions arranged on flexible arms 44. Abutting the protrusions is a retraction release ring 46, which will be described closer below. A spring 48, hereafter named penetration spring, is arranged between the retraction release ring 46 and a penetration sleeve 50. At the front end of the penetration sleeve, a retraction spring retainer 52 is snap fitted with the penetration sleeve 50 by outwardly directed protrusions 54 having a straight part and a ramped part, extending into recesses 56 of the sleeve. Outside the penetration sleeve a lockout sleeve 58 is arranged. At the rear part of the lockout sleeve 58 recesses 60 are arranged adjacent flexible arms 62 of the penetration sleeve, which arms are arranged with outwardly extending protrusions 64 as well as inwardly extending ledges 66. In the initial position these ledges are in contact with a wall of a circumferential groove 68 on the decoupling sleeve 34. The upper part of the arms 62 is further arranged with inclined surfaces 70. At the upper end of the housing an activation button 72 is slidably arranged, having inwardly extending parts 74, which are arranged with inclined surfaces facing the inclined surfaces 70 of the arms 62. Further a penetration retraction spring 76 is arranged between the retraction release ring 46 and an annular ledge 78 arranged on the decoupling sleeve 34, FIG. 5b.

Figure 4:
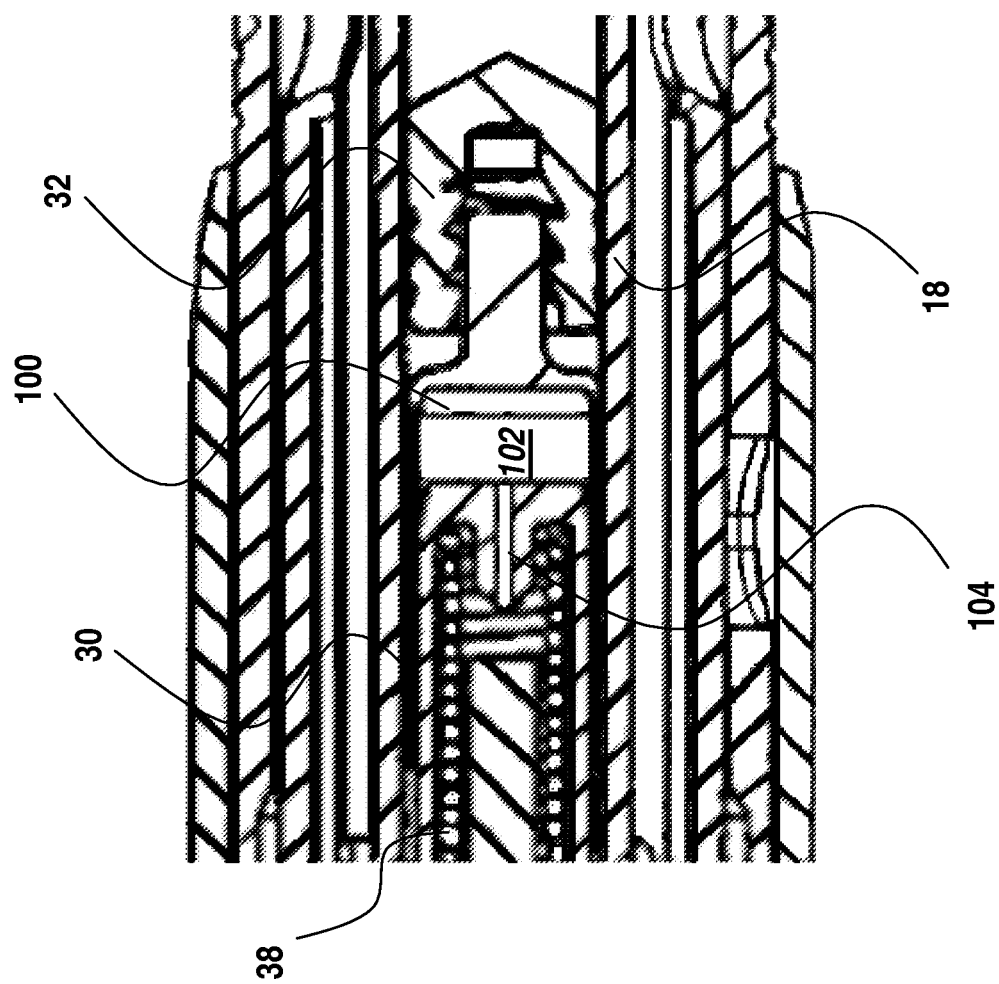
FIG. 4 shows a detailed view in cross-section of an embodiment of the present invention.

According to the invention it is further arranged with a delay mechanism, FIG. 4. It comprises a cap or cover 100 slidably arranged at the front end of the plunger rod 30. A compartment 102 created by the interior of the cap and the front surface of the plunger rod is filled with a highly viscous liquid, such as grease, oil, paste and the like. The front surface of the plunger rod is further arranged with a through-hole 104 forming a passage between the compartment and the interior of the plunger rod, the function of which will be explained below.

The device is intended to function as follows. When in the initial position the needle shield 12 is positioned inside the housing 10 and held in place by the protrusions 14 acting against the ledge of the housing, FIG. 1. The device can be delivered with a protective cap 106 inserted into the front end of the needle shield surrounding the front end of the container 18 with its container cap 78. The protective cap is removed, whereby the container cap is also removed, and a needle 22 is attached to the container. The needle shield 12 is then pushed manually forward until the protrusions 14 of the needle shield enter a recess 80 on the inner surface of the housing 10, FIG. 5a. The protrusions have such a configuration that they are able to slide over the ledge when the needle shield is extended but prevent a pushing in of the needle shield when they have entered the recess.

The device is now ready to use. The user places the end of the needle shield 12 against the injection site and presses the push button 72. The pressing of the needle shield 12 causes it to move a short distance inwards until the protrusions 14 of the needle shield abut the upper wall of the recess 80. This movement causes the lockout sleeve 58 to be moved the same short distance since the upper end of the needle shield 12 in the extended position is in contact with the lower end of the lockout sleeve 58.

If the device is withdrawn from the injection site the lockout sleeve and the needle shield are moved back to initial position. The movement of the lockout sleeve causes its recesses 60 to be positioned outside of the outwardly extending protrusions 64 of the arms 62 of the penetration sleeve 50, which enables the button 72 to be depressed whereby the inclined surfaces of the inwardly extending parts act on the inclined surfaces 70 of the arms 62, causing them to move radially outwards. This is not possible when the lockout sleeve 58 has not been moved since the protrusions of the arms then abut the inner surface of the lockout sleeve.

Figure 6:
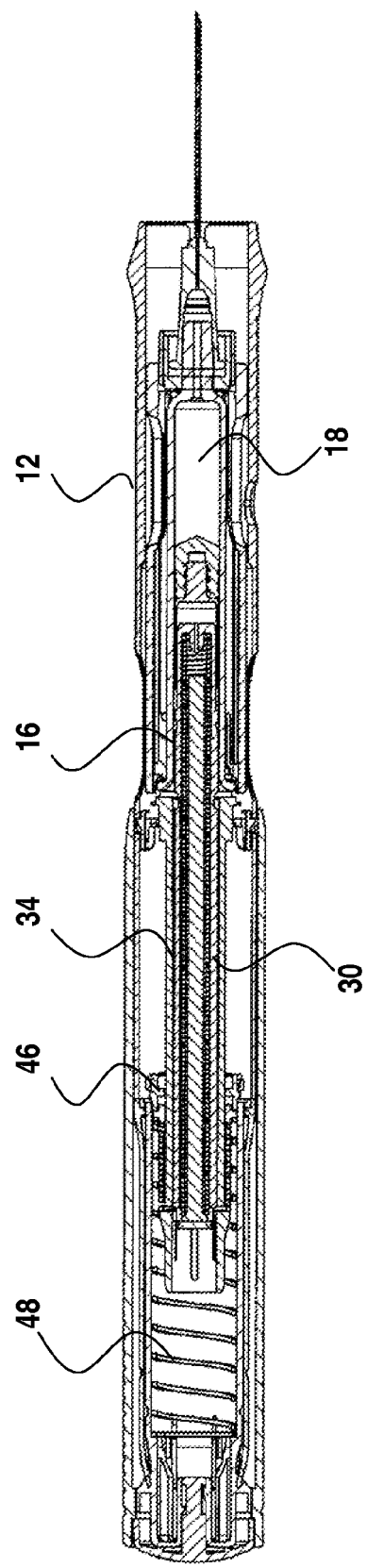

When the arms move radially outwards the inwardly directed ledges 66 of the arms 62 are moved out of contact with the circumferential groove 68 of the decoupling sleeve 34 which then is moved forward by the penetration spring 48 acting on the retraction release ring 46 which is held in place relative the decoupling sleeve 34 by the protrusions 44. Thus the decoupling sleeve 34, the plunger 30 arranged inside the decoupling sleeve, the container carrier 16 connected to the decoupling sleeve, the injection release ring 28 and the container 18 are moved forward causing a penetration of the needle into the injection site, FIG. 6.

At a certain depth the injection release ring 28 is stopped by the engagement of protrusions on its flexible arms into slots on the needle shield 12, which frees the flexible tongues 36 because they pass the ring due to the continued movement of the decoupling sleeve 34. The freeing of the tongues cause them to flex outwards radially, whereby the inwardly directed ledges are moved out of contact with the groove 37 on the plunger. The movement of the decoupling sleeve 34, and thus the penetration, is stopped when the retraction release ring 46 contacts the retraction spring retainer 52.

Figure 7:
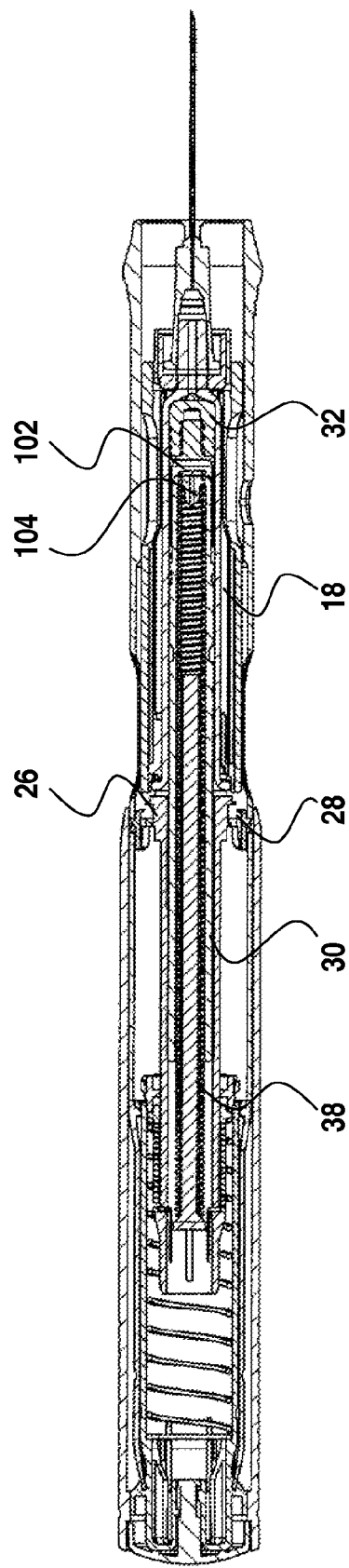

However the plunger is now free to move by the force of the injection spring 38, whereby it pushes on the stopper 32 and an injection is performed, FIG. 7. When the stopper has reached almost the front end of the container, the force of the plunger rod will act on the highly viscous liquid in the compartment 102 inside the cap 100, the force generating a displacement of the cup 100 which in turn makes the grease, or oil, to flow through the passage 104 provided by the tip of the plunger rod, FIG. 4. Grease viscosity and hydraulic diameter, size and shape of the opening of the plunger rod, are main parameters to tune to deliver the intended and desired functionality, the intended function being to achieve a time delay at stroke end so that displacement members of the system are not triggered before desired displacements, such as e.g. delivery of the drug, have been completed.

Figure 8:
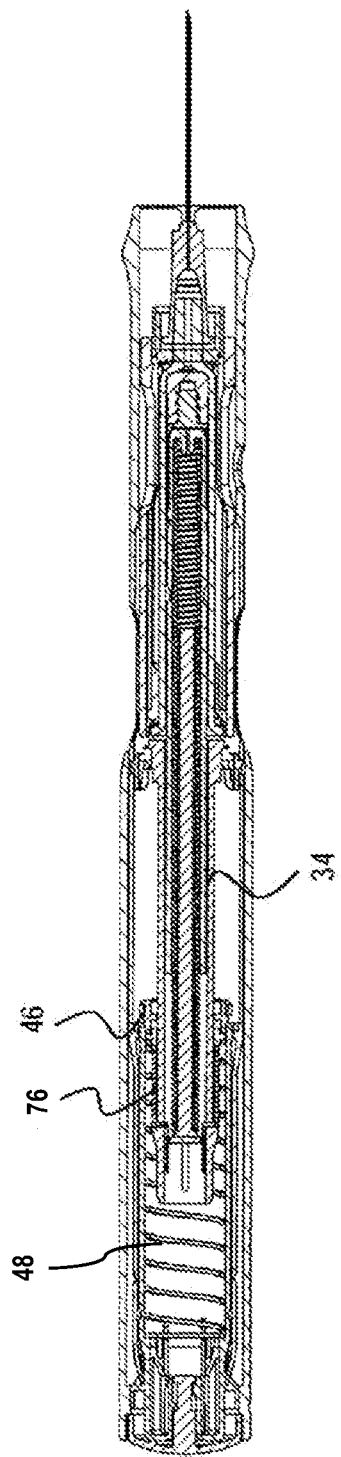

The movement of the plunger in relation to the decoupling sleeve 34 causes the upper end of the plunger to pass the protrusions 44 of the decoupling sleeve, whereby they are capable of collapsing inwards, FIG. 8.

Figure 9:
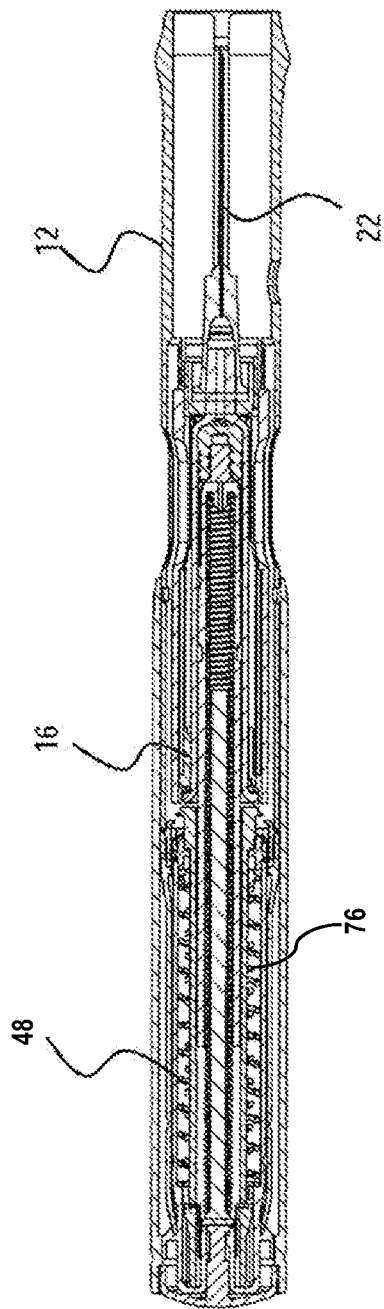
Figure 10:
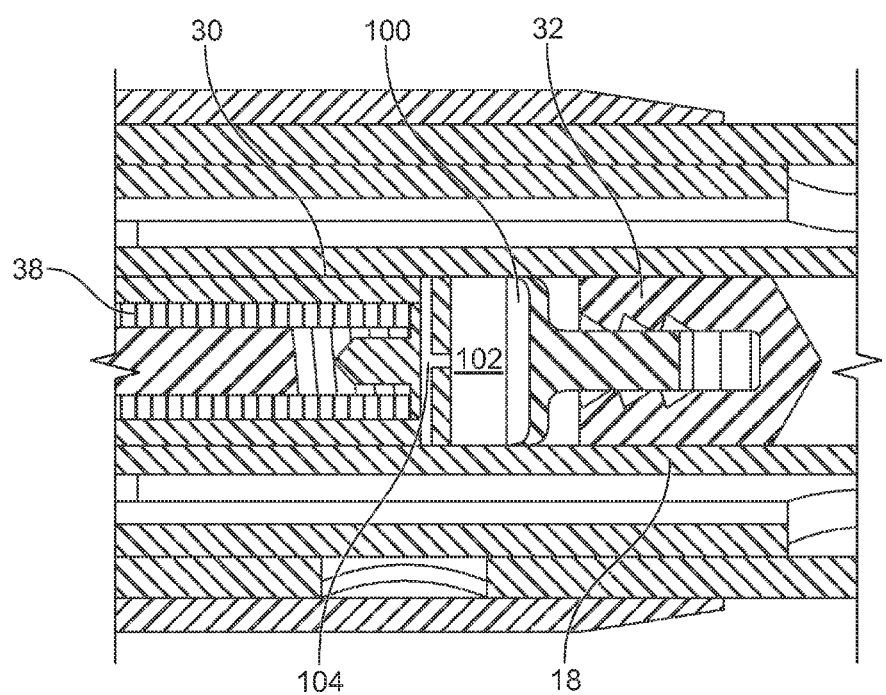
FIG. 10 illustrates the annular space created between the plunger rod and an inner surface of the medicament container of the injector of FIG. 1.

The collapsing causes the retraction release ring 46 to pass the protrusions 44 and to be pushed downwards by the retraction spring 76. This causes the container carrier 16 with the container 18 to be pulled into the housing via the decoupling sleeve 34 at near end of injection stroke, and thus the needle 22 to be retracted, FIG. 9. The injection is now completed and the needle is protected inside the housing.

The present invention could of course be used for delaying other functions of an injection device such as a delaying mechanism arranged to delay the movement of the penetration mechanism in order to ascertain that the penetration is fully completed before the injection is triggered.

It is to be understood that the embodiment described above and shown in the drawings is to be regarded only as a non-limiting example of the invention and that it may be modified within the scope of the patent claims.

The invention claimed is:
1. An injection device, comprising:
an elongated housing;
a container carrier having a medicament container to which a needle is attached;
a penetration mechanism, comprising
a decoupling sleeve, a preloaded penetration spring device capable of acting on the decoupling sleeve and thereby on the container carrier causing a sliding movement of the container and needle, and a penetration holding device configured for holding the penetration spring device in a loaded state;

an injection mechanism, comprising a plunger rod arranged to act on a stopper in the medicament container, a preloaded injection spring device configured for acting on the plunger rod for displacement of the stopper inside the container, and an injection holding device configured for holding the injection spring device in a loaded state;

a withdrawal mechanism, comprising a preloaded retraction spring arranged to act on the decoupling sleeve and thereby on the container carrier, and a withdrawal holding device configured for holding the retraction spring in a loaded state;

a penetration sequence initiating mechanism configured for acting on a penetration trigger device arranged on the decoupling sleeve for disconnecting the penetration holding device;

an injection trigger device arranged on the decoupling sleeve and configured for disconnecting the injection holding device for initiating an injection sequence when the decoupling sleeve and the plunger rod have moved to a certain position;

a withdrawal trigger device arranged on the decoupling sleeve and configured for disconnecting the withdrawal holding device for initiating a needle withdrawal when the plunger rod has moved to a certain position; and a dampening mechanism, comprising a compartment containing a volume of viscous liquid and defined in part by an outer surface of the plunger rod and an inner surface of a cap, wherein the compartment is configured with a passage through which the viscous liquid can be forced only when the injection sequence is initiated, the passage arranged on a front surface of the plunger rod, such that the dampening mechanism begins to dampen the movement of the plunger rod as the plunger rod begins to move within the medicament container.

2. The injection device of claim 1, wherein the penetration sequence initiating mechanism comprises an activation button, a penetration sleeve, a lockout sleeve, and a needle shield;

the lockout sleeve is arranged to allow the penetration sleeve to interact with the penetration trigger device for initiating the penetration sequence after the needle shield is pressed against an injection site and the push button is manually operated.

3. The injection device of claim 1, wherein the passage ends in an interior of the plunger rod.

4. The injection device of claim 3, wherein the penetration sequence initiating mechanism comprises an activation button, a penetration sleeve, a lockout sleeve, and a needle shield;

the lockout sleeve is arranged to allow the penetration sleeve to interact with the penetration trigger device for initiating the penetration sequence after the needle shield is pressed against an injection site and the push button is manually operated.

5. The injection device of claim 1, wherein the passage ends in an annular space created between the plunger rod and an inner surface of the medicament container, whereby the viscous liquid is enabled to create a dampening shear force.

6. The injection device of claim 5, wherein the penetration sequence initiating mechanism comprises an activation button, a penetration sleeve, a lockout sleeve, and a needle shield;

the lockout sleeve is arranged to allow the penetration sleeve to interact with the penetration trigger device for initiating the penetration sequence after the needle shield is pressed against an injection site and the push button is manually operated.

* * * * *